United States Patent
Han

(10) Patent No.: US 11,013,715 B2
(45) Date of Patent: May 25, 2021

(54) NANOEMULSION HYDROPHOBIC SUBSTANCES

(71) Applicant: Vertosa, Inc., Pleasanton, CA (US)

(72) Inventor: Chunxiao Han, Dublin, CA (US)

(73) Assignee: Vertosa, Inc., Pleasanton, CA (US)

( * ) Notice: Subject to any disclaimer, the term of this patent is extended or adjusted under 35 U.S.C. 154(b) by 0 days.

(21) Appl. No.: 16/206,869

(22) Filed: Nov. 30, 2018

(65) Prior Publication Data

US 2021/0015786 A1   Jan. 21, 2021

Related U.S. Application Data

(60) Provisional application No. 62/700,642, filed on Jul. 19, 2018.

(51) Int. Cl.

| A61K 9/00 | (2006.01) |
| A61K 9/107 | (2006.01) |
| A61K 47/44 | (2017.01) |
| A61K 31/352 | (2006.01) |
| A23L 33/105 | (2016.01) |
| A61K 36/185 | (2006.01) |
| A61K 47/24 | (2006.01) |
| A61K 47/26 | (2006.01) |

(52) U.S. Cl.
CPC .......... *A61K 31/352* (2013.01); *A23L 33/105* (2016.08); *A61K 9/0014* (2013.01); *A61K 9/0056* (2013.01); *A61K 9/1075* (2013.01); *A61K 36/185* (2013.01); *A61K 47/24* (2013.01); *A61K 47/26* (2013.01); *A61K 47/44* (2013.01); *A23V 2002/00* (2013.01)

(58) Field of Classification Search
None
See application file for complete search history.

(56) References Cited

U.S. PATENT DOCUMENTS

| 5,585,506 | A | * | 12/1996 | Harvey | C07C 67/08 554/173 |
| 6,541,018 | B1 | | 4/2003 | Simonnet | A61K 9/1075 424/401 |
| 9,757,701 | B2 | * | 9/2017 | Kwetkat | A61K 8/0208 |
| 9,925,149 | B2 | | 3/2018 | Kaufman | |
| 10,028,919 | B2 | | 7/2018 | Kaufman | |
| 2003/0040571 | A1 | * | 2/2003 | Feng | A61K 8/068 524/837 |
| 2005/0049230 | A1 | * | 3/2005 | Henrich | A01N 61/00 514/169 |
| 2009/0196972 | A1 | * | 8/2009 | Monsalve-Gonzalez | A23L 27/105 426/534 |
| 2012/0093896 | A1 | * | 4/2012 | Mongiat | A61Q 19/00 424/401 |
| 2012/0202891 | A1 | | 8/2012 | Stinchcomb et al. | |
| 2016/0249660 | A1 | * | 9/2016 | Langan | A23L 31/00 426/7 |
| 2016/0376263 | A1 | | 12/2016 | Patron et al. | |
| 2017/0042791 | A1 | * | 2/2017 | Ghalili | A61K 8/97 |
| 2017/0265494 | A1 | | 9/2017 | Uccello, III | |
| 2018/0020699 | A1 | * | 1/2018 | Steup | A23L 33/105 514/456 |
| 2018/0042845 | A1 | | 2/2018 | Sinai et al. | |
| 2018/0296493 | A1 | | 10/2018 | Kaufman | |
| 2018/0360704 | A1 | * | 12/2018 | Riefler | A61K 36/53 |
| 2019/0307719 | A1 | * | 10/2019 | Karelis | A61K 36/185 |

FOREIGN PATENT DOCUMENTS

| EP | 2995302 A1 | 3/2016 | |
| WO | 2009020666 A1 | 2/2009 | |
| WO | WO-2016097425 A1 * | 6/2016 | ........... A61K 31/352 |
| WO | WO-2016144376 A1 * | 9/2016 | ............... A61K 9/12 |
| WO | 2018152334 A1 | 8/2018 | |

OTHER PUBLICATIONS

Product data sheet for POLYALDO® 10-2-P, pp. 1-2. (Year: 2005).*
Komaiko et al.; "Formation of Oil-in-Water Emulsions form Natural Emulsifiers Using Spontaneous Emulsification: Sunflower Phospholipids," 2015; ACS; Journal of Agricultural and Food Chemistry, vol. 63, p. 10078-10088. (Year: 2015).*
Whitehurst, Robert J. (ed.); "Emulsifiers in Food Technology," 2004, Blackwell Publishing Ltd.; Chapter 7, pp. 162-185. (Year: 2004).*
Thakur, Ajap et al.; "Nanoemulsion in Enhancement of Bioavailability of poorly soluble drugs: A Review," 2013; Pharmacophore, vol. 4, No. 1, pp. 15-25. (Year: 2013).*
American Lecithin Company (retrieved from: americanlecithin.us/sourcing-sunflower-derived.htm on Nov. 21, 2019), pp. 1-3, as provided. (Year: 2019).*
Rupp, Christopher et al.; "Mixed Micelle formation with phosphatidylcholines: The influence of surfactants with different molecule structures," 2010; ELSEVIER, International Journal of Pharmaceutics, vol. 378, pp. 120-128. (Year: 2010).*
Tan, Chin Ping et al.; "Effect of polyglycerol esters of fatty acids on physicochemical properties and stability of β-carotene nanodispersions prepared by emulsification/evaporation method," 2004, Soc. Chem. Indust.; Journal of the Science of Food and Agriculture, vol. 85, pp. 121-126. (Year: 2004).*
Metcalf, Katy L. et al.; "Taste Intensities of Oil-in-Water Emulsions with varying fat content," 2002, Journal of Sensory Studies, vol. 17, Iss. 5, pp. 379-390. (Year: 2002).*
Fakruddin Md, "Biosurfactant: Production and Application," J. Pet. Environ. Biotechnol., 2012; 3(4): 5 pgs.
Pacwa-Plociniczak, et al., "Environmental Applications of Biosurfactants: Recent Advances," International Journal of Molecular Sciences, 2011; 12:633-654.

* cited by examiner

Primary Examiner — David J Blanchard
Assistant Examiner — Ivan A Greene
(74) Attorney, Agent, or Firm — Plant & Planet Law Firm

(57) ABSTRACT

Disclosed herein are compositions, having nanosized droplets, wherein the nanosized droplets may contain a cannabinoid oil, a dietically acceptable carrier oil, a surfactant, and water. Also disclosed herein are methods of making and using the same.

15 Claims, 11 Drawing Sheets

Size distribution for emulsion system A

Size distribution for emulsion system B

Nanoemulsion droplet physical stability at 0.1mg/g, pH=8 environment and 55°C

Figure 6

Nanoemulsion droplet physical stability at 0.1mg/g, pH=3.5 environment and 55°C

Fresh made Sample 4 weeks stored at 4°C

Figure 8.

| Sample | Repeats | CBG (mg/g) | CBD (mg/g) | CBN (mg/g) | THC (mg/g) | Standard Diviation | |
|---|---|---|---|---|---|---|---|
| 1 x HH221 | #1 | 0.643 | 4.386 | 0.086 | 19.938 | 0.0049 | Raw Emulsion |
| | #2 | 0.648 | 4.389 | 0.084 | 19.932 | | |
| | #3 | 0.645 | 4.399 | 0.081 | 19.944 | | |
| 10 x HH221 | #1 | 0.063 | 0.469 | 0.000 | 1.991 | 0.0021 | Topical |
| | #2 | 0.062 | 0.477 | 0.000 | 1.989 | | |
| | #3 | 0.063 | 0.473 | 0.000 | 1.986 | | |
| 100 x HH221 | #1 | 0.000 | 0.042 | 0.000 | 0.196 | 0.0017 | High Dose |
| | #2 | 0.000 | 0.048 | 0.000 | 0.193 | | |
| | #3 | 0.000 | 0.044 | 0.000 | 0.197 | | |
| 500 x HH221 | #1 | 0.000 | 0.000 | 0.000 | 0.039 | 0.0005 | Low Dose |
| | #2 | 0.000 | 0.000 | 0.000 | 0.038 | | |
| | #3 | 0.000 | 0.000 | 0.000 | 0.038 | | |

NANOEMULSION HYDROPHOBIC SUBSTANCES

CROSS REFERENCE TO RELATED APPLICATIONS

This application claims the benefit of priority to U.S. Provisional Application Ser. No. 62/700,642 filed Jul. 19, 2018, the entire contents of which is incorporated herein by reference.

FIELD OF THE INVENTION

The field of the invention is cannabinoid emulsions.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

There are many ways to administer medical and recreational cannabis. One common problem with currently available cannabinoid compositions and methods of administration is that cannabinoids are not water soluble and therefore only a small percentage of the consumed cannabinoid content is absorbed by the human body. Moreover, because cannabinoids are not water soluble, it is difficult to put it in common foods and drinks. Finally, the low aqueous solubility also contributes to lower potency and slower onset of action in lower doses.

Nanoparticles comprising cannabis are one way to improve solubility. For example, US20180296493A1 to Richard Clark Kaufman teaches a nanosphere compositional structure comprising encapsulated cannabinoid. PCT/US2017/049219 discloses a cannabinoid nanoemulsoin made from surfactant Vitamin E TPGS. US20120202891A1 discloses a gel comprising cannabis nanoparticles, and US20170265494 discloses a chewing gum having a liquid center and the liquid center comprises "nanozome" encapsulated cannabinoid. However, in each of the above methods, the stability of such nanoparticles disclosed is less than desirable, especially upon dilution in an aqueous carrier. Moreover, at least some nanoparticle formulations tend to suffer from particle aggregation. Finally, the taste of the cannabinoid nanoparticles also remains unknown.

Thus, there remains a need in the art for new compositions of cannabinoid that remain dispersed in water and thereby leads to higher potency, faster onset of action, and have a pleasant taste such that it can be easily added to common foods and drinks.

SUMMARY OF THE INVENTION

Various embodiments disclosed herein are drawn towards cannabinoid nano-emulsion compositions, methods, and kits, comprising: a cannabinoid oil, a dietically acceptable carrier oil, at least one surfactant, and water. In preferred embodiments, the amount of water is at least 1.15 times the amount of the combination of the cannabinoid oil, the dietically acceptable carrier oil, and the surfactant. In preferred embodiments, the amount of the dietically acceptable carrier oil is contemplated to be at least 0.3 times the amount of the cannabinoid oil. Furthermore, in some embodiments, the amount of the surfactant is at least 1.45 times the amount of cannabinoid oil, and/or the amount of surfactant is at least 1.35 times the amount of carrier oil, and/or the amount of surfactant is at least 1.15 times the amount of combination of cannabinoid oil and carrier oil.

The at least one surfactant contemplated herein may comprise a tween surfactant, a polyglyceryl surfactant, a long chain PEG surfactant, or combinations thereof. The amount of the surfactant in the composition depends on the hydrophilic-lipophilic balance (HLB). If the HLB of the surfactant is >13, then the amount of the surfactant is at least 0.65 times the amount of the combination of the cannabinoid oil and the dietically acceptable carrier oil; if the HLB of the surfactant is between 11 and 13, then the amount of the surfactant is at least 0.8 times the amount of the combination of the cannabinoid oil and the dietically acceptable carrier oil; and if the HLB of the surfactant is between 8.5 and 11, then the amount of the surfactant is at least 0.95 times the amount of the combination of the cannabinoid oil and the dietically acceptable carrier oil;

The composition may have one or more surfactants. When there are two surfactants, say a main surfactant and a co-surfactant, and the amount of the main surfactant is at least 1.05 times the amount of combination of cannabinoid oil and carrier oil. The co-surfactant is contemplated to be a small molecule food surfactant, a natural lecithin, a purified lecithin, or combinations thereof. If the co-surfactant is a natural lecithin, then the amount of the co-surfactant is at least 0.75 times the amount of the dietically acceptable carrier oil; if the co-surfactant is a purified lecithin, then the amount of the co-surfactant is at least 0.50 times the amount of the dietically acceptable carrier oil; and if the co-surfactant is a small molecule food emulsifier, then the amount of the co-surfactant is at least 0.80 times the amount of the dietically acceptable carrier oil.

The cannabinoid oil in the composition may comprise a phyto-cannabinoid or a synthetic cannabinoid. The composition may further comprise one or more preservatives, a flavoring agent, a bitter blocker, an essential oil and/or a terpene.

The average diameter or Z-average of the nano-emulsions in the composition is preferably smaller than 100 nm, when tested by Dynamic Light Scattering, and in some cases, about 80% of the nano-droplets in the composition are contemplated to have a droplet size between 30-50 nm. Notably, the composition disclosed herein may be a liquid composition. The composition remains in dispersed form upon dilution in aqueous solution. The droplet size remains unaffected upon dilution in aqueous solution. The composition can be stored at room temperature for at least 6 months, or in a 55° C. oven for up to 12 weeks, without change in droplet size.

In another aspect, disclosed herein is a method of making a nano-emulsion composition comprising: mixing a cannabinoid oil, a dietically acceptable carrier oil, a main surfactant, a co-surfactant; adding water to the composition and mixing to form a coarse emulsion; and inputting energy by sonication, high shearing or microfluidic droplet generating into the mixture under temperature control until the nano-emulsions are formed. The temperature of the mixture is kept below 75° C. during the mixing process.

In another aspect, disclosed herein is a method of using a nano-emulsion composition comprising: administering the composition by inhalation, targeting systemic, parenteral, oral, intrathecal, intraarticular, nasal, ophthalmic and/or topical means, wherein the nano-emulsion composition comprises a cannabinoid oil, a dietically acceptable carrier oil, a main surfactant, a co-surfactant and water. The composition is contemplated to be added to a beverage or food prior to oral administration.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 6 illustrates, in accordance with the embodiments herein, droplet physical stability over time in pH=3.5 buffer solution.

FIG. 8 illustrates, in accordance with the embodiments herein, the high repeatability and reliability of nano-emulsion potency result tested at different concentrations, detected by HPLC-DAD.

DETAILED DESCRIPTION

Figure 1:
FIG. 1 illustrates, in accordance with the embodiments herein, (A) a currently available macroemulsion cannabinoid product dispersed in water and its droplet size distribution, compared with (B) the newly disclosed nanodroplet cannabinoid composition dispersed in water and its droplet size distribution.
Figure 1:
Figure 1:
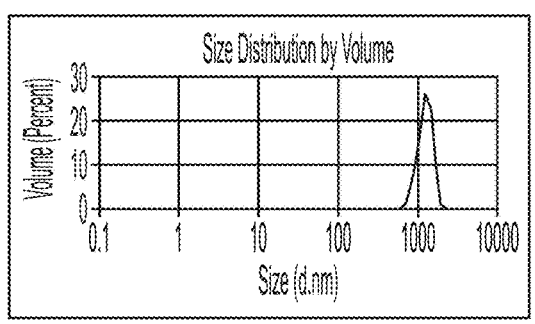
Figure 1:
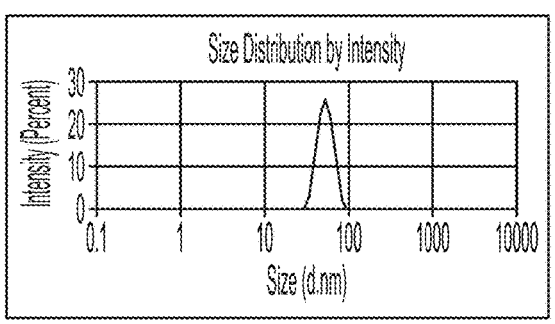

The instant subject matter is directed towards compositions, kits, and methods comprising nanosized droplets, wherein the nanosized droplets comprise a hydrophobic substance, a dietically acceptable carrier oil, a surfactant or surfactant system, and a phospholipid form. Contemplated compositions and methods overcome the current problems with cannabinoids—most current products available are macro emulsions which have drawbacks such as long-term instability, short shelf life, slow on-set time, unappealing taste and appearance, and due to its un-even distribution in water over time and often times tend to stick to the inner surface of container, the potency and homogeneity test often fail. The compositions disclosed herein overcome these problems, and as discussed herein, have fast onset time, long term stability, long shelf life, compatible with various container materials and a more controlled result on potency test. The droplet size remains stable over time and upon dilution.

The compositions provided herein have several advantages over the currently available cannabinoid compositions. In terms of onset time or bioavailability, upon smoking cannabis, only 2-45% of THC can be absorbed by lung; upon eating cannabis, only 8-15% of THC can be absorbed and it is also slow to react. One advantage of the nanosized droplet composition provided herein is the high bioavailability and fast onset, which occurs because the large surface area of these nanosized droplets easily attach to mucus surface and works on the body instantly. For example, in one embodiment, upon consuming 10 mg of the composition comprising THC as disclosed herein, an adult human subject felt lightheaded in about 10 minutes, euphoria in about 20 minutes, hunger in about 37 minutes, and happy (laughing and dancing) in about 40 minutes. Furthermore, in some embodiments, the lecithin in the composition may form a bilayer structure, called liposome, which traps the THC inside. In other embodiments, the lecithin sits on the edge of the oil droplets. Lecithin can help quicker absorption of the cannabinoid into the body. In one embodiment, onset time may depend on body size and whether the stomach is empty or full. Empty stomach often gives a much faster onset time.

The inventive subject matter provides new nano-emulsion compositions comprising: a cannabinoid oil, a dietically acceptable carrier oil, a surfactant, and water, wherein the amount of water is at least 1.15 times the amount of the combination of the cannabinoid oil, the dietically acceptable carrier oil, and the surfactant; and wherein the amount of the dietically acceptable carrier oil is at least 0.3 times the amount of the cannabinoid oil. In some embodiments, the composition may comprise more than one surfactant, such as a main surfactant and a co-surfactant. The terms "nano-droplet" and "nano-emulsion" are used interchangeably in this disclosure, and refers to dispersions or droplets comprising water, oil, and surfactant(s), as well as other lipid structures that can form as a result of hydrophobic forces that drive apolar residues (example, long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases.

As further described throughout this disclosure, the hydrophilic-lipophilic balance (HLB) of the surfactant plays an important role in determining its amount in the composition. If the HLB is >13, then the amount of the surfactant, or the main surfactant if there are more than one surfactant in the composition, is at least 0.65 times the amount of the combination of the cannabinoid oil and the dietically acceptable carrier oil. In one embodiment, if the HLB of the surfactant, or the main surfactant if there are more than one surfactant in the composition, is between 11 and 13, then the amount of the main surfactant is at least 0.8 times the amount of the combination of the cannabinoid oil and the dietically acceptable carrier oil. In one embodiment, if the HLB of the surfactant, or the main surfactant if there are more than one surfactant in the composition, is between 9 and 11, then the amount of the main surfactant is at least 0.95 times the amount of the combination of the cannabinoid oil and the dietically acceptable carrier oil. The compositions provided herein have higher potency, faster onset of action, and can be easily added to common foods and drinks.

The average droplet size in the composition is less than 100 nm, either at raw emulsion level and/or at the diluted level, for example, 0.1 mg/g. In some cases, 80% of the droplets have a droplet size between 10-70 nm, or more preferably a droplet size of 30-50 nm. The size and stability of the droplet does not vary with dilution or time, and the composition can be stored at room temperature for at least 12 months, or preferably at least 18 months, or more preferably at least 24 months, or more preferably at least 30 months, or most preferably at least 36 months without change in droplet size.

The cannabinoid may be a naturally occurring phytocannabinoid or a synthetic cannabinoid. The cannabinoid may be Tetrahydrocannabinol (THC) or Cannabidiol (CBD), any other single cannabinoids or combinations thereof. The purity of the cannabinoid can be low pure (full plant distillate) or high pure (distillate). In one embodiment, the cannabinoid is selected from Tetrahydrocannabinolic acid A (THCA-A), Tetrahydrocannabinolic acid B (THCA-B), Tetrahydrocannabinol (THC), Tetrahydrocannabinolic acid C (THCA-C), Tetrahydrocannbinol C (THC-C), Tetrahydrocannabivarinic acid (THCVA), Tetrahydrocannabivarin (THCV), Tetrahydrocannabiorcolic acid (THCA-C), Tetrahydrocannabiorcol (THC-C), Delta-7-cis-iso-tetrahydrocannabivarin, A-tetrahydrocannabinolic acid (A8-THCA), A-tetrahydrocannabinol (A-THC), Cannabidiolic Acid (CBDA), Cannabidiol (CBD), Cannabidiol monomethyl ether (CBDM), Cannabidiol-C (CBD-C), Cannabidivarinic Acid (CBDVA), Cannabidivarin (CBDV), Cannabidiorcol (CBD-C), Cannabigerolic Acid (CBGA), Cannabigerolic Acid monomethylether (CBGAM), Cannabigerol (CBG), Cannabigerol monomethylether (CBGM), Cannabigerovarinic Acid (CBGVA), Cannabigerovarin (CBGV), Cannabichromenic Acid (CBCA), Cannabichromene (CBC), Cannabichromevarinic Acid (CB CVA), Cannabichromevarin (CBCV), Cannabicyclolic acid (CBLA), Cannabicyclol (CBL), Cannabicyclovarin (CBLV), Cannabielsoic acid A (CBEA-A), Cannabielsoic acid B (CBEA-B), Cannabielsoin (CBE), Cannabinolic acid (CBNA), Cannabinol (CBN), Cannabinol methylether (CBNM), Cannabinol-C (CBN-C), Cannabivarin (CBV), Cannabino-C (CBN-C), Cannabiorcol (CBN-C), Cannabinodiol (CBND), Cannabinodivarin (CBDV), Cannabitriol (CBT), 10-Ethoxy-9-hydroxy-A"-tetrahydrocannabinol, 8.9-Dihydroxy-A'-tetrahydrocannabinol (8.9-Di-OH CBT-C), Cannabitriolvarin (CBTV), Ethoxycannabitriolvarin (CBTVE), Dehydrocannabifuran (DCBF), Cannbifuran (CBF), Cannabichromanon (CBCN), Cannabicitran (CBT), 10-Oxo-A'-tetrahydrocannabinol (OTHC), A-cis-tetrahydrocannabinol (cis-THC), Cannabiripsol (CBR), 3,4,5,6-tetrahydro-7-hydroxy-alpha-alpha-2-trimethyl-9-n-propyl-2,6-methano-2H-1-benzoxocin-5-methanol (OH-iso-HHCV), Trihydroxy-delta-9-tetrahydrocannabinol (triCH-THC), Isocanabinoids, Epigallocatechin gallate, or combinations thereof.

The dietically acceptable carrier oil may comprise plant derived oils or animal derived oils. Plant derived oils contemplated in the composition include sunflower oil, olive oil, coconut oil, sesame oil, avocado oil, palm oil, soybean oil, corn oil, peanut oil, canola oil, grape seed oil, corn oil, hazelnut oil, rice bran oi, linseed oil, safflower oil, sesame oil, passion fruit oil or combinations thereof. The dietically acceptable carrier oil may also comprise animal derived oils, including lard, butter, animal fats or combinations thereof.

The surfactant may comprise one surfactant or a mixture of surfactants. For example, the surfactant may be a high molecular weight main surfactant and a co-surfactant of lower molecular weight. The main surfactant may be a tween surfactant, a polyglyceryl surfactant, and/or a long chain PEG surfactant. In one embodiment, the tween surfactant may be selected from the group consisting of Tween 20, Tween 40, Tween 45, Tween 60, Tween 65, Tween 80, Tween 81 and Tween 85. In one embodiment, the polyglyceryl surfactant is selected either from polyglyceryl monoesters or polyglyceryl multi-esters. Examples of polyglyceryl monoesters contemplated herein include Polyglyceryl-4 Caprate, Polyglyceryl-4 Caprylate, Polyglyceryl-4 Laurate, Polyglyceryl-4 Isostearate, Polyglyceryl-4 Oleate, Polyglyceryl-5 Laurate, Polyglyceryl-5 Myristate, Polyglyceryl-5 Isostearate, Polyglyceryl-5 Oleate, Polyglyceryl-5 Stearate, Polyglyceryl-6 Isostearate, Polyglyceryl-6 Oleate, Polyglyceryl-6 Stearate, Polyglyceryl-8 Oleate Polyglyceryl-8 Stearat, Polyglyceryl-10 Laurate, Polyglyceryl-10 Myristate, Polyglyceryl-10 Palmitate, Polyglyceryl-10 Isostearate, Polyglyceryl-10 Linoleate, Polyglyceryl-10 Oleate, Polyglyceryl-10 Stearate, Polyglyceryl-10 Behenate/Eicosadioate, Polyglyceryl-10 Hydroxystearate/Stearate/Eicosadioate and Polyglyceryl-10 fatty ester (POLYALDO® 10-2-P). Polyglyceryl multi-esters contemplated in the composition disclosed herein include Polyglyceryl-5 Triisostearate, Polyglyceryl-5 Dioleate, Polyglyceryl-5 Trioleate, Polyglyceryl-6 Tricaprylate, Polyglyceryl-6 Dioleate, Polyglyceryl-6 Distearate, Polyglyceryl-6 Pentastearate, Polyglyceryl-6 Octastearate, Polyglyceryl-8 Decaerucate/Decaisostearate/Decaricinoleate, Polyglyceryl-10 Caprylate/Caprate, Polyglyceryl-10 Dipalmitate, Polyglyceryl-10 Diisostearate, Polyglyceryl-10 Pentaisostearate, Polyglyceryl-10 Nonaisostearate, Polyglyceryl-10 Decaisostearate, Polyglyceryl-10 Dioleate, Polyglyceryl-10 Pentaoleate, Polyglyceryl-10 Decaoleate, Polyglyceryl-10 Distearate, Polyglyceryl-10 Tristearate, Polyglyceryl-10 Pentastearate, Polyglyceryl-10 Pentahydroxystearate, and/or Polyglyceryl-10 Heptahydroxystearate.

In some embodiments, the long chain PEG surfactant is preferably a non-ionic surfactant sold under the trademark BRIJ®. Examples include BRIJ® CS20 (Ceteareth-20, Polyoxyethylene (20) Cetyl Stearyl Ether), BRIJ® C10 (Ceteth-10, Polyoxyethylene (10) cetyl ether), BRIJ® C20 (Ceteth-20, Polyoxyethylene (20) cetyl ether), BRIJ® IC20 (Isoceteth-20, Alkoxylated ether), BRIJ® IC20-70 (Isocetech-20 (Alkoxylated ether) and Aqua), BRIJ® L4 (Laureth-4, Ethoxylated Fatty Alcohol), BRIJ® L23 (Laureth-23, Polyoxyethylene (23) lauryl ether), BRIJ® L23-69 (Laureth-23 (Polyoxyethylene (23) lauryl ether) and Aqua), BRIJ® O10 (Oleth-10, Polyoxyethylene (10) oleyl ether), BRIJ® O20 (Oleth-20, Polyoxyethylene (20) oleyl ether), BRIJ® S10 (Steareth-10, Polyoxyethylene (10) stearyl ether), BRIJ® S20 (Steareth-20, Polyoxyethylene (20) stearyl ether), BRIJ® S100 (Steareth-100, Polyoxyethylene (100) stearyl ether) and/or BRIJ® S721 (Steareth-21, ethoxylated fatty alcohols).

The co-surfactant is preferably a small molecule food surfactant, a natural lecithin, a purified lecithin, or combinations thereof. The small molecule food surfactant may comprise Span 20, Span 40, Span 60, Span 80, Span 83, Span 85, Span 120, Glyceryl Laurate, and/or Glyceryl Stearate Citrate. The natural lecithin, if present, may be extracted from soybean, eggs, milk, marine sources, rapeseed, cottonseed, and/or sunflower seed. Purified lecithin, when present may comprise Lipoid S 40, Lipoid H 50, Lipoid PHOSAL® 50 SA, Lipoid PHOSAL® 53 MCT, Lipoid P 75, Lipoid S 75, Lipoid S 80, Lipoid E 80, PHOSPHOLIPON® 85 G, Lipoid PHOSPHOLIPON® 90 G, Lipoid PHOSPHOLIPON® 90 H, and/or Lipoid H 100.

In one embodiment, the inventor was surprised to find that while Span 20 generated a nano-emulsion composition where the droplet size was less than 100 nm, Span 40, Span 60, Span 80, Span 83, Span 85, and Span 120 generated emulsions with droplet size larger than 100 nm.

In some embodiments of the composition disclosed herein, if co-surfactant is a raw lecithin, then the amount of the co-surfactant is at least 0.75 times the amount of the dietically acceptable carrier oil; wherein if co-surfactant is a purified lecithin, then the amount of the co-surfactant is at least 0.50 times the amount of the dietically acceptable carrier oil; and wherein if co-surfactant is a small molecule food emulsifier, then the amount of the co-surfactant is at least 0.80 times the amount of the dietically acceptable carrier oil.

Phospholipids may also be present in the composition, for example lecithin such as those extracted from soybean, eggs, milk, marine sources, rapeseed, cottonseed, and/or sunflower seed.

The composition may further comprise a preservative and/or an essential oil, or a terpene or a flavoring agent or a food color or a bitter blocker or an artificial flavor agent. The purpose is to improve taste and appearance of the composition.

In another aspect, the present disclosure provides a method of making the compositions disclosed herein, comprising: mixing the hydrophobic substance, the dietically acceptable carrier oil, surfactants or co-surfactants, and phosphorus lipid form; adding water to the composition and mixing to form a coarse emulsion; and sonicating the mixture under temperature control until the nanosized droplets are formed. The temperature of the mixture is usually kept below 75° C. during the mixing process. The method may further include sterilizing the composition, for example, by filtering it.

The instant disclosure also describes a method of using a nano-emulsion composition comprising administering the composition by inhalation, targeting systemic, parenteral, oral, intrathecal, intraarticular, nasal, ophthalmic and/or topical means, wherein the nano-emulsion composition comprises a cannabinoid oil, a dietically acceptable carrier oil, a main surfactant, a co-surfactant and water. Thus, the various compositions disclosed herein may be used by adding it to a food or beverage, or may be used to consume directly. All compositions can be applied in topicals, cosmetics or personal lubricant products.

In another preferred aspect, disclosed herein is a nano-emulsion composition comprising: a cannabinoid oil, a dietically acceptable carrier oil, a main surfactant, a co-surfactant, and water, wherein the amount of water is at least 1.15 times the amount of the combination of the cannabinoid oil, the dietically acceptable carrier oil, the main surfactant, and the co-surfactant, and wherein the amount of the dietically acceptable carrier oil is at least 0.3 times the amount of the cannabinoid oil. Within the same surfactant family, when the main surfactants have similar structures, hydrophilic-lipophilic balance (HLB) can help determine the relative ratios needed to make nano-emulsions. For example, within the same surfactant category, if the HLB of the main surfactant is >13, then the amount of the main surfactant is at least 0.65 times the amount of the combination of the cannabinoid oil and the dietically acceptable carrier oil; if the HLB of the main surfactant is between 11 and 13, then the amount of the main surfactant is at least 0.8 times the amount of the combination of the cannabinoid oil and the dietically acceptable carrier oil; and if the HLB of the main surfactant is between 9 and 11, then the amount of the main surfactant is at least 0.95 times the amount of the combination of the cannabinoid oil and the dietically acceptable carrier oil.

The hydrophilic-lipophilic balance (HLB) of a surfactant is a measure of the degree to which it is hydrophilic or lipophilic. The HLB value can be used to predict the surfactant properties of a molecule. For example, HLB of less than 10 indicates lipid-soluble (water-insoluble), while an HLB of more than 10 indicates water-soluble (lipid-insoluble). Generally, an oil in water emulsifier has HLB of 8 to 16, while a solubilizer or hydrotope has a HLB of 16 to 18. HLB's of some commonly known compounds are illustrated below in Table 1. It should be noted that the HLB of a compound would be known to a skilled artisan in the art, and the list below is illustrative purposes only, and it is not meant to be an exclusive list of compounds that many be used as a surfactant for the compositions and methods disclosed herein. Furthermore, as would be known to a skilled artisan in the art, HLB is best applied to compare within the same surfactant family, and comparing HLB values between two different surfactant families often will not generate expected results.

HLB is calculated as $HLB = 20 * M_h / M$ where $M_h$ is the molecular mass of the hydrophilic portion of the molecule, and M is the molecular mass of the whole molecule, giving a result on a scale of 0 to 20. Table 1 shows HLB of some surfactant used in this patent.

TABLE 1

| Compound | HLB |
| --- | --- |
| polyglyceryl-6 oleate | 9 |
| Polyglyceryl-6 Stearate | 9 |
| Polyglyceryl-6 Laurate | 14.5 |
| Polyglyceryl-6 caprylate | 15 |
| Glyceryl Stearate | 3.8 |
| Oleth-20 | 15.3 |
| Steareth-20 | 15.3 |
| Steareth-21 | 15.5 |
| Ceteth-20 | 15.7 |
| Tween 20 | 16.7 |
| Tween 21 | 13.3 |
| Tween 40 | 15.6 |
| Tween 60 | 14.9 |
| Tween 61 | 9.6 |
| Tween 65 | 10.5 |
| Tween 80 | 15 |
| Tween 81 | 10 |
| Tween 85 | 11 |

In one embodiment, the inventor was surprised to find that the droplet size of the composition disclosed herein is higher than 100 nm when the main surfactant is from Polyglyceryl-4 Series, including Polyglyceryl-4 Caprate, Polyglyceryl-4 Caprylate, Polyglyceryl-4 Laurate, Polyglyceryl-4 Isostearate, and Polyglyceryl-4 Oleate. It may be due to their relatively lower HLBs compared to Polyglyceryl-6 or Polyglyceryl-10 Series. When 1 g of cannabinoid oil, 0.7 g of olive oil, 2.5 g of a Polyglyceryl-4 surfactant, 1.5 g of lecithin with sunflower, and 40 g of water, were mixed and sonicated at 80% amplitude, the Polyglyceryl-4 surfactants failed to make a nano-emulsion. Droplet size change was monitored by DLS time wise. Sonication was stopped when droplet size reach plateau and does not decrease. The final emulsion droplet average size obtained with Polyglyceryl-4 Caprate, Polyglyceryl-4 Caprylate, Polyglyceryl-4 Laurate, Polyglyceryl-4 Isostearate, and Polyglyceryl-4 Oleate were 365 nm, 427 nm, 488 nm, 371 nm, and 506 nm respectively. This unexpected result illustrated that while some surfactants result in the desired claimed nano-emulsion composition, other surfactants may not. It should be noted, however, that while the Polyglyceryl-4 series of surfactants failed to make a nano-emulsion, they may be utilized when a larger droplet size is desired.

Throughout the following discussion, numerous references are made regarding cannabinoid compounds or cannabinoid derivatives. It should be noted that while the general discussion is towards cannabinoids, the instant composition can also be used for any other hydrophobic compounds that would benefit from dispersing in an aqueous solution, including terpenes, other essential oils, extract from herbs, eicosapentaenoic acid (EPA) and/or docosahexaenoic acid (DHA) or many other hydrophobic drug molecules.

Figure 2:
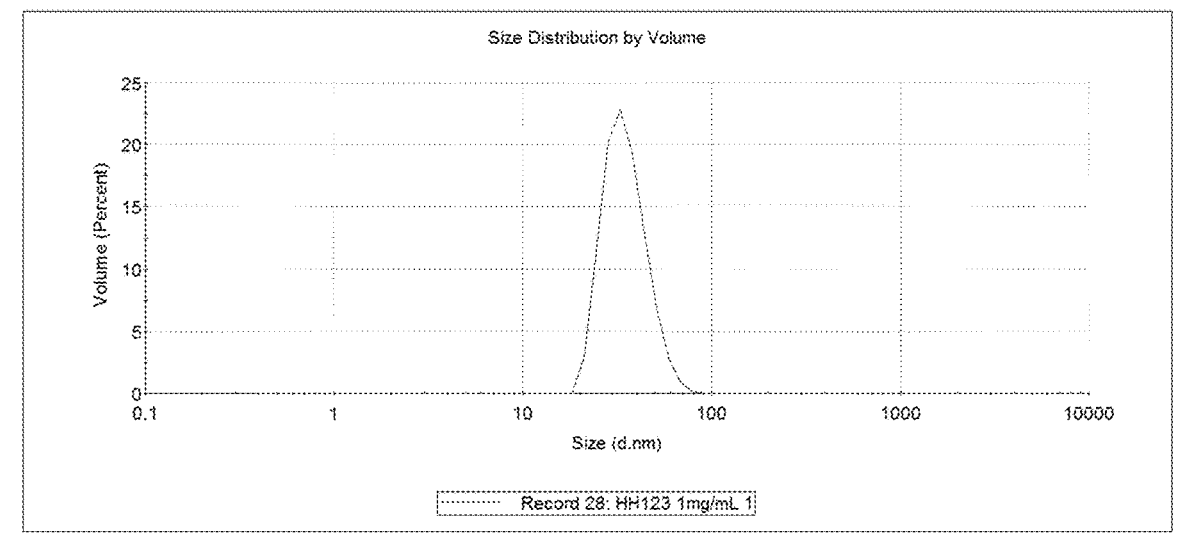
FIG. 2 illustrates, in accordance with the embodiments herein, initial emulsion droplet size of the composition disclosed herein. The initial emulsion concentration was kept at 25 mg/mL.
Figure 3:
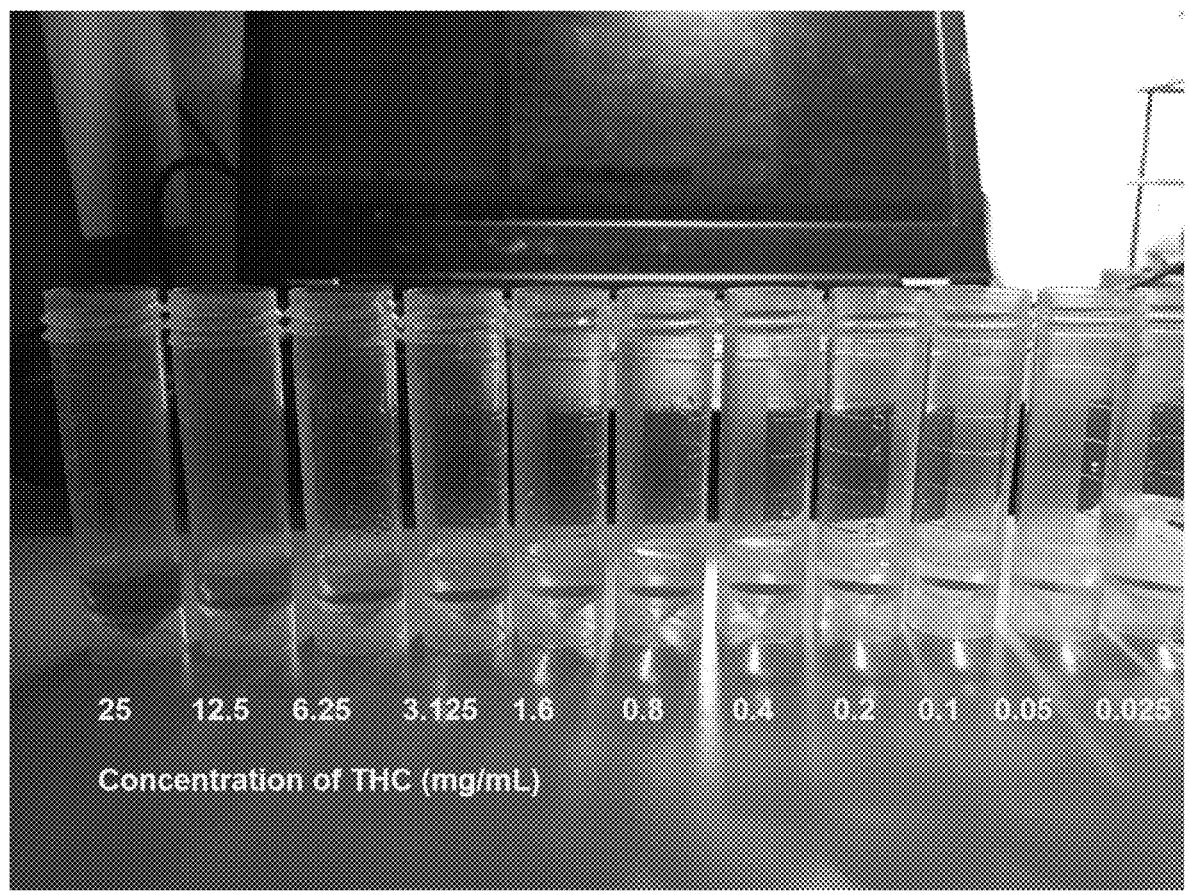
FIG. 3 illustrates, in accordance with the embodiments herein, that no precipitation was observed upon dilution of concentrated composition. The concentrated composition can be diluted by any fold to make the final product.
Figure 4:
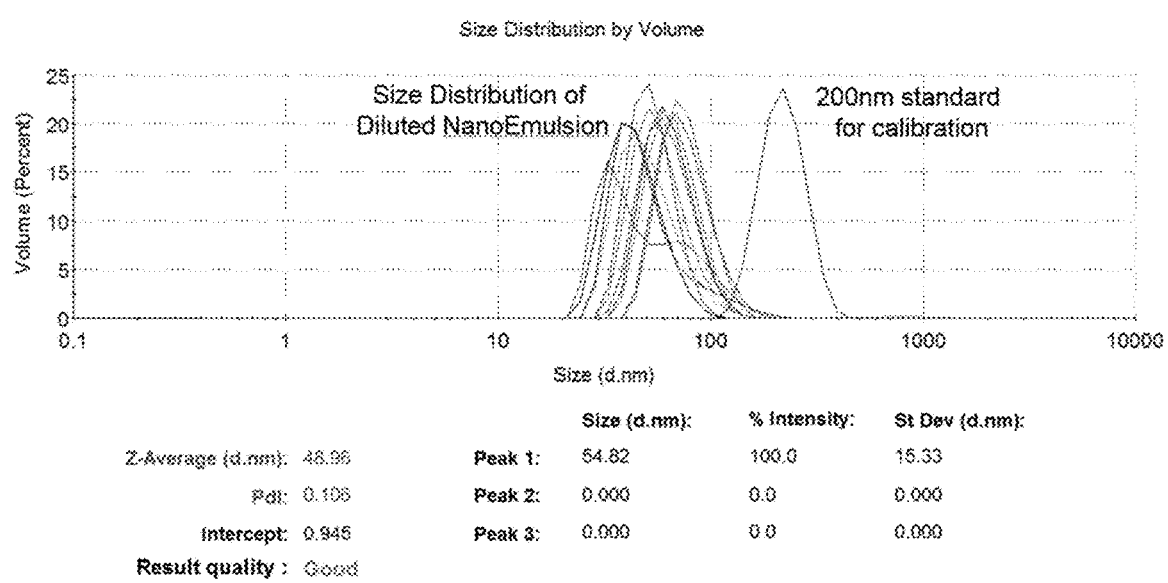
FIG. 4 illustrates, in accordance with the embodiments herein, nanosized emulsion droplets does not change its size upon dilution.
Figure 5:
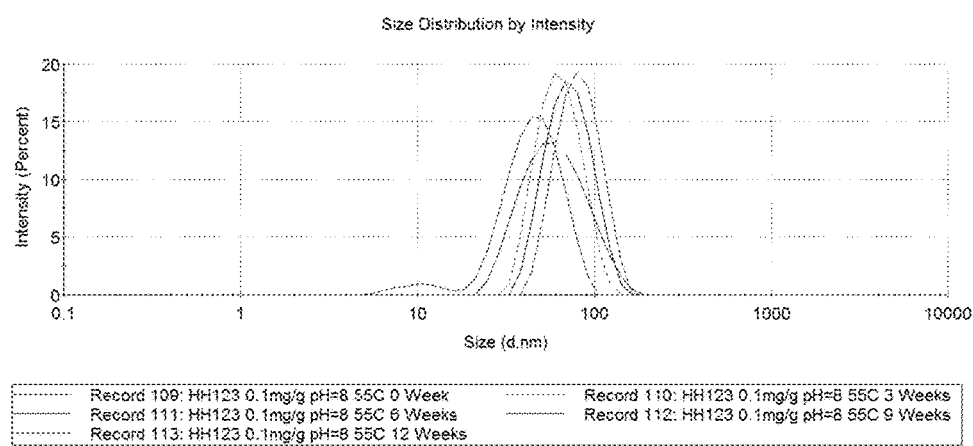
FIG. 5 illustrates, in accordance with the embodiments herein, droplet physical stability over time in pH=8 buffer solution.
Figure 7:
FIG. 7 illustrates, in accordance with the embodiments herein, emulsion stability under refrigerated conditions over four weeks, no reversed phase transformation or precipitates observed. And it also showed the emulsion is compatible with polypropylene plastic material.
Figure 7:
Figure 7:
Figure 7:
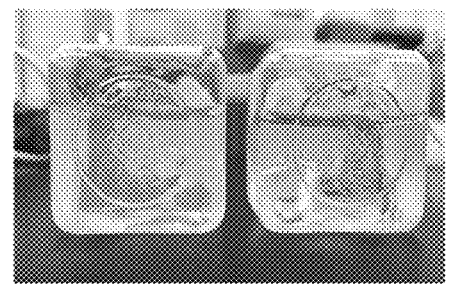

In the various embodiments disclosed herein, the average nanosized droplet size is less than 500 nm. In some cases, the average droplet size is 400 nm, or less than 200 nm, or less than 100 nm, or less than 90 nm, or less than 80 nm, or less than 70 nm. In one preferred embodiment, at least 80% of the nanosized droplets in the composition have a droplet size between 10-70 nm, or between 30-50 nm, as illustrated in FIGS. 2 and 4. In some cases, the average nanosized droplet is 35 nm with a standard deviation of 10 nm, as illustrated in FIG. 2. When the composition is diluted the average nanosized droplet is 46 nm with a standard deviation of 15 nm, as illustrated in FIG. 4. Sometimes, measuring concentrated nano-emulsion (>10 mg/g) by Dynamic Light Scattering could have misleading data. Since at higher concentration, the emulsion droplets pack close to each other and may generate unreal scattering pattern. Emulsion concentration at 0.1 mg/g (of active ingredient) is usually used as the standard measuring concentration. While the nanosized droplets are a preferred embodiment of the instant application, larger sized droplets are contemplated as well. Sometimes, larger size emulsion is generated by design to achieve desirable effects.

n one aspect, the composition disclosed herein is preferably a liquid composition. The composition remains in dispersed form upon dilution in aqueous solution, as illustrated in FIG. 3. As shown in FIG. 4, the droplet size remains unaffected upon dilution in aqueous solution. As shown in FIG. 5, the composition, after dilution into pH 8 solution, can be stored at room temperature (calculated from 55° C. acceleration study) for up to three years without change in droplet size. FIG. 6 demonstrated the composition, after diluted into pH 3.5 solution, also have up to equivalent to three years of stability at room temperature (calculated from 55° C. acceleration study). Table 2 shows the stability correlation relation between 55° C. and room temperature.

TABLE 2

| Stability at 55° C. | Equivalent shelf life at Room Temperature |
|---|---|
| 1 week | 3 month |
| 3 week | 9 month |
| 6 week | 18 month (1.5 years) |
| 9 week | 27 month |
| 12 week | 36 month (3 years) |

Since the nano-emulsion can be diluted to any concentration and remain the integrity of nano-sized droplets, it can be applied in various different applications where different concentration of active ingredient is needed. For example, Table 3 shows possible end applications the nano-emulsion can apply to:

TABLE 3

| Final cannabinoid concentration (mg/g) | Product types that is suitable at this concentration |
|---|---|
| 12.5 | High concentration topicals |
| 6.25 | High concentration tinctures |
| 3.125 | Topicals or lubricants |
| 1.6 | Facial creams |
| 0.8 | Directly used cannabis shot |
| 0.4 | Flavored cannabis Shot |
| 0.2 | Beverages for medical patients |
| 0.1 | High dose beverages |
| 0.05 | Low dose beverages |
| 0.025 | Micro-dosing beverages |

The hydrophobic substance of the composition disclosed herein preferably comprises a plant extract. In especially preferred embodiments, the hydrophobic substance comprises a cannabinoid. The cannabinoid may be a phytocannabinoid or a synthetic cannabinoid, as disclosed above.

In some embodiments, the nanosized droplets may comprise more than one hydrophobic substance. In some instances, it is contemplated that the more than one hydrophobic substance will have synergistic effect with each other to produce a result that is better than the sum of its parts. For example, by way of example, each nanosized droplet in the composition may comprise THC, CBD and a terpene compound. The amounts of each component in the droplet may be controlled. For example, in some embodiment, each nanosized droplet may have 1×THC, 3×CBD, and 4× Terpene. As is generally known in the art, THC, CBD, terpene, together with other cannabinoid compounds, have synergistic effect, they often have better results compared to just consuming one compound. Furthermore, the droplet may have another flavoring agent, such as mint oil, orange oil or lemon oil. Thus, the cannabis oil may be infused with any other oil in the nano-emulsion form. Thus, in one embodiment, by using this method, different kinds of nano-emulsions may be prepared from different plant extract; and these nano-emulsions may be used in a drink to mimic the natural effect of the plant, or even create other special effect which is not available from natural plants themselves.

The composition disclosed herein also comprises an edible carrier oil. The edible carrier oil as contemplated herein may be from the plant material, which comprises sunflower oil, olive oil, coconut oil, sesame oil, avocado oil, palm oil, soybean oil, corn oil, peanut oil, canola oil, or combinations thereof. The edible oil may also be from animal parts, such as for example, lard or butter.

The composition also typically includes one or more surfactant. When more than one surfactant is used, preferably one is a high molecular weight surfactant and the other is a low molecular weight surfactant. Thus, in one case, the surfactant comprises a main surfactant and a co-surfactant, wherein the main surfactant is a high molecular weight surfactant, and the co-surfactant is a lower molecular weight surfactant. The compositions described herein may further comprise a preservative and/or a flavoring agent. The preservative, if present, is usually between 0-2% of the composition. In one example, the preservative is citric acid and/or benzoic acid. The preservative system can also be natural compounds like Vitamin E and Vitamin C. The flavoring agent may be an essential oil, such as for example, Lemon oil, orange oil, peppermint oil, Ylang Ylang oil, Lemon Grass oil, Tea Tree oil, Rosemary oil, Australian Sandalwood oil, Grape fruit oil, frankincense oil, cedarwood oil, patchouli oil, cinnamon bark oil, bergamot oil, chamomile oil, Lemon Eucalyptus oil, ginger oil, key lime oil, vanilla oil and/or clove oil. The flavoring agent, if present, comprises about 1-10% of the composition.

The compositions disclosed herein may also comprise different types of bitter blockers. Synthetic or natural bitter blockers can be used in cannabinoid nano-emulsions to block bitterness that originated from un-pure plant extracts, wax, polyphenols or undesired flavors from surfactant systems. The bitter blockers used in the compositions disclosed herein include BB68 (3-[1-[(3,5-dimethylisoxazol-4-yl)methyl]pyrazol-4-yl]-1-[(3-hydroxyphenyl)methyl]imidazolidine-2,4-dione) from Senomyx, GG-605-390-4, NP-844-232-9 and QJ-615-696-6 from Givaudan, TRUCLEAR™ from Tastesnaturel and/or CLEARTASTE™ from MycoTechnology. BB68 was introduced either by ethanol or polypropylene glycol into the final nano-emulsion system at the concentration range from 2.5-10 ppm, depending on the certain bitterness of diluted emulsion. GG-605-390-4, NP-844-232-9 and QJ-615-696-6 were directly added into the diluted nano-emulsion at concentration range from 0.01%-0.05%. TRUCLEAR™ and CLEARTASTE™ can be used at the concentration of 0.001-0.1%, depending on nano-emulsion's composition. Sometimes, different bitter blockers can be mixed and used together, for example, 0.015% NP-844-232-9 plus 0.015% GG-605-390-4 has a better effect on flavor compared to using 0.03% GG-605-390-4 or 0.03% NP-844-232-9 along. It should be noted that all those bitter blockers can also be added into the raw emulsion at higher concentration, so that when the raw emulsion get diluted into final drinks, the bitter blockers' concentration can reach to the level mentioned above.

The compositions disclosed herein may comprise various amounts of the hydrophobic substance, the dietically acceptable carrier oil, the surfactant, and the phospholipid form as described above. One non-limiting composition include: 10-20% of cannabis oil, 5-15% of sunflower oil, olive oil or coconut oil, 60-70% of Tween 80, and 5-15% of sunflower lecithin. Another non-limiting composition include: 10-20% of cannabis oil, 5-15% of sunflower oil, olive oil or coconut oil, 60-70% of Tween 20, and 5-15% of sunflower lecithin.

By way of example, a composition disclosed herein having a tween series main surfactant would have about 1 part by mass of the cannabinoid oil, 0.35-3 parts carrier oil, 2-4 parts main surfactant of the Tween series, 0.5-3.5 parts co-surfactant, and 30 parts water. Similarly, when a composition disclosed herein has a tween series main surfactant and a natural lecithin as a co-surfactant would have about 1 part by mass of the cannabinoid oil, 0.35-3 parts carrier oil, 1.75-4 parts main surfactant of the Tween series, 0.5-3.5 parts natural lecithin, and 30 parts water. When the composition comprises a main surfactant tween series and a purified lecithin as a co-surfactant, the composition would have about 1 part by mass of the cannabinoid oil, 0.35-3 parts carrier oil, 1.2-3 parts main surfactant of the Tween series, 0.85-3 parts purified lecithin, and 30 parts water.

By way of another example, for a composition disclosed herein having a polyglyceryl series main surfactant would have about 1 part by mass of the cannabinoid oil, 0.35-3 parts carrier oil, 1.75-3.5 parts main surfactant of the polyglyceryl series, 1-3.5 parts co-surfactant, and 30 parts water. Similarly, when a composition disclosed herein has a polyglyceryl series main surfactant and a natural lecithin as a co-surfactant would have about 1 part by mass of the cannabinoid oil, 0.35-3 parts carrier oil, 1.9-4 parts main surfactant of the polyglyceryl series, 0.5-3.5 parts natural lecithin, and 30 parts water. When the composition comprises a main surfactant polyglyceryl series and a purified lecithin as a co-surfactant, the composition would have about 1 part by mass of the cannabinoid oil, 0.35-3 parts carrier oil, 1.5-4 parts main surfactant of the polyglyceryl series, 0.85-3 parts purified lecithin, and 30 parts water.

By way of a further example, for a composition disclosed herein having a long chain PEG series main surfactant would have about 1 part by mass of the cannabinoid oil, 0.35-3 parts carrier oil, 1.25-3.75 parts main surfactant of the long chain PEG series, 0.5-3 parts co-surfactant, and 30 parts water. Similarly, when a composition disclosed herein has a long chain PEG series main surfactant and a natural lecithin as a co-surfactant would have about 1 part by mass of the cannabinoid oil, 0.35-3 parts carrier oil, 1.75-4 parts main surfactant of the long chain PEG series, 0.35-3 parts natural lecithin, and 30 parts water. When the composition comprises a main surfactant long chain PEG series and a purified lecithin as a co-surfactant, the composition would have about 1 part by mass of the cannabinoid oil, 0.35-3 parts carrier oil, 1-3 parts main surfactant of the long-chain PEG series, 0.85-3 parts purified lecithin, and 30 parts water.

No matter using which main surfactant category is selected, carrier oil can sometimes exceed cannabinoid oil by many folds, as long as the following criteria is met, nano-emulsion can still be produced: main surfactant is at least 1.05 times the amount of combination of cannabinoid oil and carrier oil and if the co-surfactant is a natural lecithin, then the amount of the co-surfactant is at least 0.75 times the amount of the dietically acceptable carrier oil; if the co-surfactant is a purified lecithin, then the amount of the co-surfactant is at least 0.50 times the amount of the dietically acceptable carrier oil; and if the co-surfactant is a small molecule food emulsifier, then the amount of the co-surfactant is at least 0.80 times the amount of the dietically acceptable carrier oil.

Figure 9:
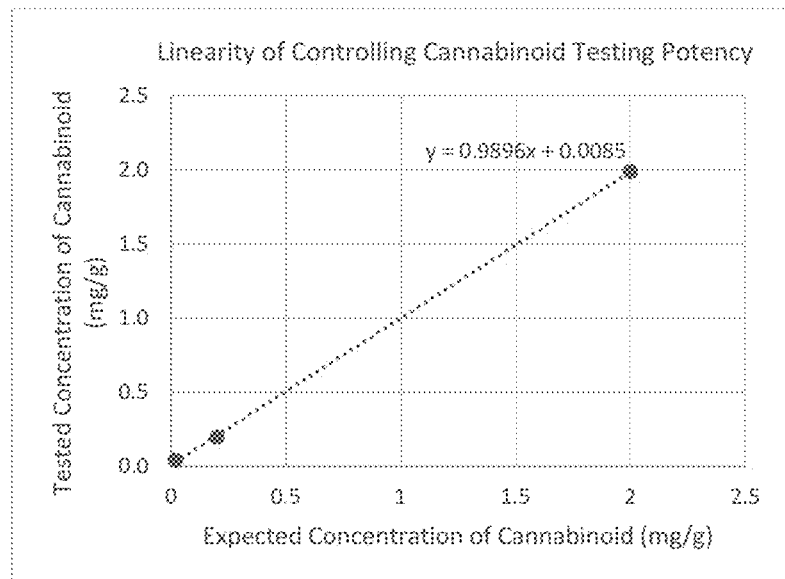
FIG. 9 illustrates, in accordance with the embodiments herein, linearity of potency control uses the nano-emulsion.
Figure 10:
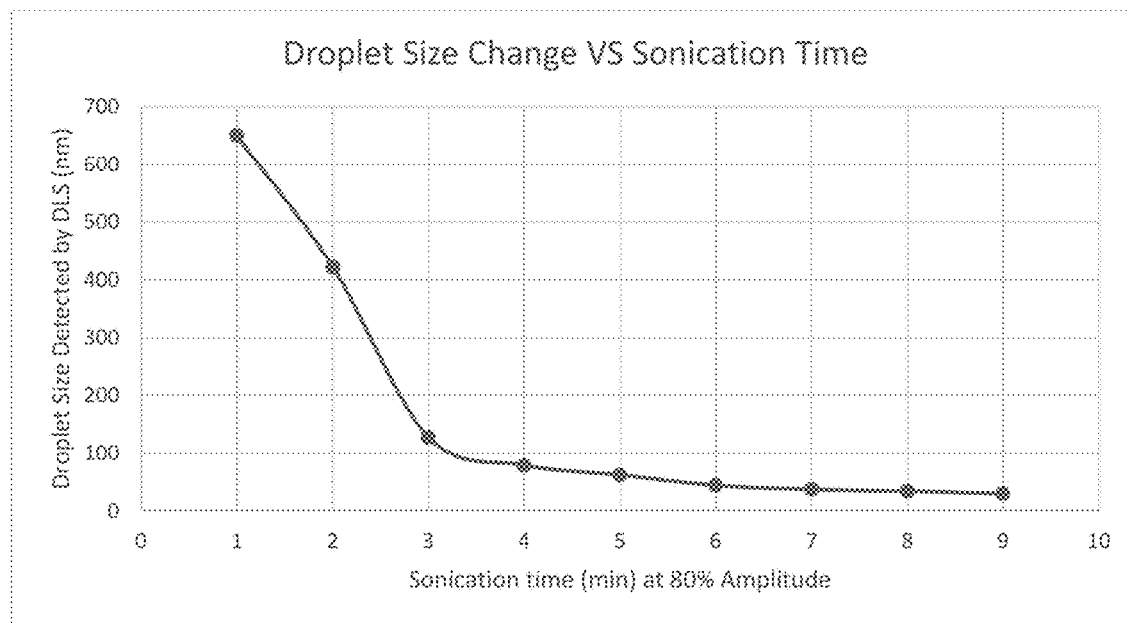
FIG. 10 illustrates, in accordance with the embodiments herein, droplet size change over sonication time. Smaller size can be obtained by higher energy input.
Figure 11:
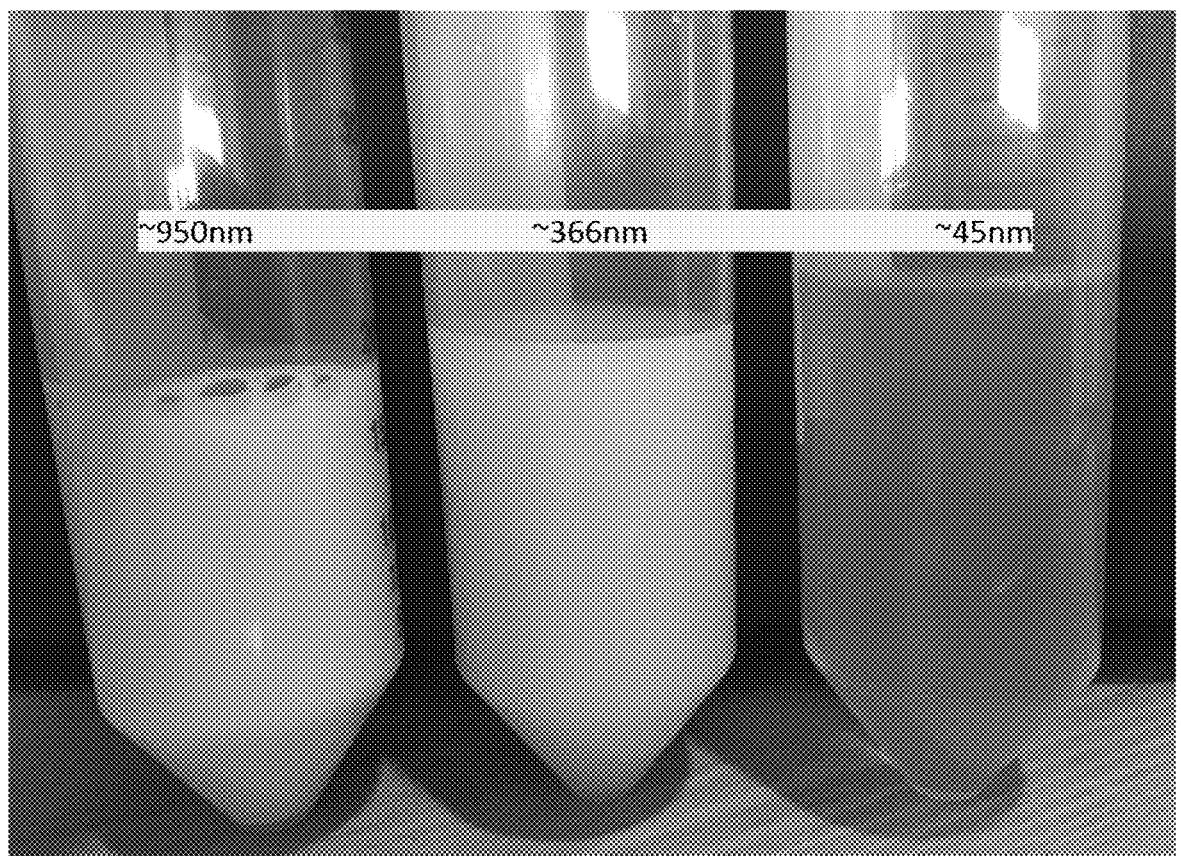
FIG. 11 illustrates, in accordance with the embodiments herein, the appearance of the concentrated nano-emulsion at different droplet size distributions, which can be controlled and obtained by altering the sonication amplitude and time.

As is generally known in the art, droplet sizes and their distribution may affect the human feeling on flavor. On one side, nano-size can amplify or even alter the taste, something tastes plain at bulk may taste bitter or sour in nano-scale. On the other side, taste buds on tongue tend to have different time reactions to different sizes of particles. The smaller droplets can quickly absorb at the gap of the tasting buds, thus blocking the touching/feeling from bigger droplets. The droplet size can be well controlled by how much energy is put into the liquid system, which can be controlled either by amplitude % of the sonicator or by how long the liquid is being sonicated at certain amplitude %. For example, shown in FIG. 10, 8-10 mins of sonication at 80% amplitude can generate an average of 30 nm olive oil nano-emulsion, while 4-5 mins of sonication at 80% amplitude can generate an average of 70 nm cannabinoid nano-emulsion.

It would be generally known to a skilled artisan in the art that ultrasonic frequency of a sonicator is generally fixed at 20 kHz and does not fluctuate during sonication. The sonicator continuously calibrates itself to ensure consistent output. A commercially available sonicator may be used to make the compositions disclosed herein. The wattage of such a sonicator may vary from 250 W to about 800 W, and more preferably between about 350 W to about 650 W, and most preferably between 450 W to about 550 W. The output energy depends on the viscosity of the emulsion and also temperature. For example, when the formula contains enough amount of surfactant and enough amount of water, the total energy required to generate nano-emulsion (J/mL) will be less than a formula that contains less surfactants and less water, which is due to how easy it is for the droplet to form in the emulsion and viscosity. Processing amplitude are adjustable, and it is within a linear relation with intensity. And process time can also be adjustable, which will determine total input energy under certain intensity. Since each formula may need different amount of energy to get into nanosize, we usually monitor droplet size change with Dynamic Light Scattering over production time to determine when to stop the sonication.

There are two major methods to operate sonication: batch mode and continuous mode. For batch size less than 200 mL, batch mode is applied, which includes a sonication probe immersed into the target liquid. For batch size larger than 1 L, continuous mode is preferred, where the raw emulsion was stored in a tank, and it gets pumped into the sonication chamber and pumped back into the tank. The energy input happens at the sonication chamber. Usually, in preferred embodiments, the whole volume of liquid would be circulated 12-20 times to achieve nanosize. For example, for a 10 L tank, under 2 L per min pumping rate, the amount to time needed to generate a nano-emulsion is calculated as follows: (12-20)×10 L/2 L/mins=60-100 mins.

Heat is generated during the sonication process, overheat not only damage equipment, but also will degrade cannabinoid. For batch mode, ice/dry ice batch is applied to maintain the temperature. For continuous mode, recirculating chillers were applied to cool down the reaction chamber during the process. The temperature was kept below 70° C. for both modes.

In one aspect, provided herein is a method of making a composition comprising: mixing the hydrophobic substance, the dietically acceptable carrier oil, surfactant, and phosphorus lipid form; adding water to the composition and mixing to form an emulsion; and sonicating the mixture under temperature control until the nanosized droplets are formed. The temperature of the mixture is usually kept below 75° C. during the mixing process. In some instances, the composition is sterilized by filtering through a 0.2 um filter. The composition is usually stored in a light blocking vessel and stored at 4° C. If larger droplets are desired for a particular application, for example microsized droplets, the energy put in during the mixing process is lowered.

The compositions disclosed herein may be administered to a subject in a variety of ways, such as, for example, by inhalation, targeting systemic, parenteral, oral, intrathecal, intraarticular, nasal, ophthalmic and/or topical means. In one embodiment, the compositions disclosed herein may be added to a beverage or food prior to oral administration. The compositions may be used for an application that uses aqueous infusion, say for example, water-based lube, chewing gum, topicals, facial spray, makeup remover etc. The technology of nanosized particles may also be used for other applications, for example, pharmaceutical drug delivery of a hydrophobic drug, or general food and agriculture material treatment.

Viewed from a different perspective, the compositions disclosed herein may be grouped as systems; each such system is discussed in detail below. Each system contains target oil (cannabis oil in particular), carrier oil, one to three surfactant types, and water. The major differences between systems are the combination of surfactant types and its relative amount to other ingredients.

System 1: Polyglyceryl Series Surfactant+Co-Surfactant

Polyglyceryl surfactant series are generally regarded to be very safe to consume, there is usually no upper limit of consumption in food. Its main structure contains a polyglycerol chain as hydrophilic head and a fatty acid as hydrophobic tail. The co-surfactants applied here can be small molecule food emulsifiers, natural lecithin or purified lecithin. In a typical formula, the total mass amount of polyglycerol surfactant plus co-surfactant should be higher than twice the total mass amount of target oil plus carrier oil. In some cases, the mass amount of co-surfactant should be higher than the mass amount of carrier oil. The relative ratio of polyglyceryl surfactant used in the system can be determined by its HLB, as disclosed herein.

System 2: Long Chain PEG (BRIJ®) Series Surfactant+Co-Surfactant

BRIJ® surfactants are widely used in cosmetic products due to their excellent surface activity. BRIJ® surfactant can be used in combination of co-surfactant to make cannabinoid nano-emulsion. Co-surfactant in this system can be small molecule food emulsifiers, natural lecithin and/or purified lecithin. In a typical formula, the total mass amount of BRJI surfactant plus co-surfactant should be higher than twice the total mass amount of target oil plus carrier oil. In some cases, the mass amount of co-surfactant should be higher than the mass amount of carrier oil. The relative ratio of BRIJ® surfactant used in the system can be determined by its HLB, which is disclosed in herein.

System 3: Tween Surfactant with Co-Surfactant:

Polysorbate (Tween) surfactants are commonly used in food and cosmetic industry due to their high surface property and relative safety to human consumption. It includes Tween 20, Tween 40, Tween 45, Tween 60, Tween 65, Tween 80 and Tween 85. They share the same hydrophilic head, the only difference lays in their hydrophobic chain in terms of chain length and saturation. The Tween family system can be used with various co-surfactants to generate nanoemulsions.

In general, tween surfactant's amount in mass should be higher than 0.65 times the total weight of target oil and carrier oil, and co-surfactant's amount in mass should be higher than 0.80 times the weight of carrier oil. The total amount of tween surfactant plus the co-surfactant should be higher than 1.85 times of weight of target oil, and/or 1.35 times the weight of carrier oil and/or 1.15 times the total weight of target oil and carrier oil. Below are 7 examples from the system 3 using Tween surfactants and co-surfactant.

System 4: Combination of Different Main Surfactants

Sometimes, a combination of different types of main surfactants, can also generate cannabinoid nano-emulsions. The main surfactant types include polyglyceryl series, tween series and/or BRIJ® series. The ratio of different types of main surfactants can be adjusted to any desired range as long as the amount of combination of main surfactants should be at 1.05 times the amount combination of cannabinoid oil and carrier oil. For example, the main surfactants can be split into half as Tween Series and half as polyglyceryl Series, or ⅓ as Tween Series, ⅓ as polyglyceryl Series and ⅓ as BRIJ® series. As long as their total amount is greater than 1.05 times the amount combination of cannabinoid oil and carrier oil.

The description throughout this disclosure provides many example embodiments of the inventive subject matter. Although each embodiment represents a single combination of inventive elements, the inventive subject matter is considered to include all possible combinations of the disclosed elements. Thus, if one embodiment comprises elements sunflower oil, tween-80, sunflower lecithin, and cannabinoid, and a second embodiment comprises elements coconut oil, tween-20, sunflower lecithin, cannabinoid and lemon oil, then the inventive subject matter is also considered to include other remaining combinations of sunflower oil, coconut oil, tween-80, tween-20, sunflower lecithin, cannabinoid, and lemon oil, even if not explicitly disclosed.

Embodiments of the present disclosure are further described in the following examples. The examples are merely illustrative and do not in any way limit the scope of the invention as claimed.

EXAMPLES

Example 1

Formula 1 with a General Base Formula

The formula 1 disclosed below is a general base formula that works with many starting materials. This composition has a bitter taste due to the presence of Tween-80. The bitter taste may be desirable in some cases. If the bitter taste is not desired, then additives such as essential oils may be added to mask the bitter taste.

Formula 1.

| Items | Mass (g) | Mass Ratio |
|---|---|---|
| Sunflower oil or olive oil or solid coconut oil or liquid coconut oil | 0.625 | 1 |
| Tween 80 | 2.5-4.5 | 4-7.2 |
| Sunflower lecithin | 0.625-0.9 | 1-1.44 |
| Citric acid or benzoic acid (optional, not active) | 0.001 or 0 | |

1 g of cannabis and 5 g of the Formula 1 are added to a 100 ml beaker, and mechanically stirred under controlled heat (<60° C.), until it is well mixed. The cannabis oil may be a full plant extract or a high pure distillate. Water is added to the mixture, the amount of water is determined by the final targeting concentration. The mixture is kept stirring until a homogenous milky coarse emulsion is formed. The mixture is put in an ice bath and a sonicator probe is inserted into the liquid. The mixture is sonicated at 80% amplitude. Temperature of the liquid should be constantly monitored, when temperature is above 70° C., the sonication should be stopped, let the liquid cool down to room temperature and restart the sonication until the liquid become translucent/transparent (nanoemulsion). Sometimes, in order to further improve the taste, finished nanoemulsion will flow through a packed $Al_2O_3$ or activated charcoal column. The nanoemulsion is then filtered through a nylon 0.2 um filter, collected in a light blocking vessel, and kept at 4° C.

The concentration ranges of ingredients above represent a scenario where nano-emulsion can be generated. In the meanwhile, depending on final target droplet sizes, the ingredients' concentration ranges can be flexible. For example, if nano-emulsion is target (<100 nm), then the desirable range of each ingredient can be: cannabinoids (1 g), carrier oil (0.5-2 g), Tween 80 (2.5-4.5 g) and lecithin (0.3-3 g). Tween 80 is the major driving force in the formula, with enough of it, the final formulation can be driven into nano-size. Another example, if an emulsion with droplet size in the range over 100 nm is desired, the desirable range of each ingredient can be: cannabinoids (1 g), carrier oil (0.5-6 g), Tween 80 (1-2 g) and lecithin (0.3-3 g).

The above formula 1 is a general base formula to which different ingredients can be added to suit the needs of a particular application. For example, the ingredients and the amounts may be varied to vary onset time, flavor, look, stability, compatibility, concentration, texture. For example, a water lube needs to have a good taste, a good smell, and a high concentration of cannabinoid and a low droplet size distribution to allow the cannabinoid to absorb quicker, also need to keep the texture of product to be viscous and smooth. Thus, in this example, the concentration of cannabinoid in the nano-emulsion would be higher, since only a small volume of nano-emulsion can be added to the lube base. Furthermore, it is noted that while oil may break down a latex condom, the carrier oil or essential oil in the formula will have no such effect because oil is trapped inside the tiny droplets, which is protected by the surfactants on the edge as an insulating layer. This protection effect is better when the surfactant hydrophilic heads are bigger, which offer more room for the protection layer.

Example 2

Formula 2 that Works with High Purity Distillate and is Less Bitter than Formula 1

The formula 2 disclosed herein works with most high purity distillate cannabis oil. It is less bitter than Formula 1 due to the incorporation of Tween 20 instead of Tween 80. Similar to formula 1, 1 g of cannabis oil is mixed with 5 g of the formula 2 and the method disclosed above for formula 1 is used to making the composition. The desirable concentration range of Formula 2 is similar to the Formula 1 as described above.

Formula 2.

| Items | Mass (g) | Mass Ratio |
|---|---|---|
| Sunflower oil or olive oil or solid coconut oil or liquid coconut oil | 0.625 | 1 |
| Tween 20 | 2.5-4.5 | 4-7.2 |
| Sunflower lecithin | 0.625-0.9 | 1-1.44 |
| Citric acid or benzoic acid (optional, not active) | 0.001 or 0 | |

Example 3

Formula 3 with Higher Quantity of Carrier Oils

Formula 3 can tolerate more carrier oil and still generate nanoemulsions of cannabinoids. The carrier oil can be fats from animal parts, such as lard or butter, or from plants, such as sunflower oil, liquid coconut oil or any other forms. Similar to above, 1 g of cannabis oil (either full plant extract or high pure distillate) is added to 6 g of natural fats first, stir and heat is applied to make sure the natural fats and cannabinoids are fully mixed into one continuous phase.

Then, 7 g of Tween 20 and 1.2 g of Sunflower lecithin were added into the oil mixture. In one embodiment, the method disclosed above for formula 1 is used to making the instant composition.

Each ingredient's concentration range is determined by the target needs. In one embodiment, for example, for each 1 g of THC distillate, 6 g of fats are used. Under this combination, Tween 20 range can be anywhere from 6-8.5 g and sunflower lecithin range can be anywhere from 4.68-6 g. As long as main surfactant and co-surfactant amount increase together with the carrier oil following the rule as below, cannabinoid nanoemulsion can be generated: amount of the total surfactants is at least 1.45 times the amount of cannabinoid oil, and/or the amount of total surfactants is at least 1.35 times the amount of carrier oil, and/or the amount of total surfactants is at least 1.15 times the amount of combination of cannabinoid oil and carrier oil. THC distillates can be obtained from different purification methods, which will contribute different portion of polyphenols in the product. In this case, the other components' ranges can be Tween 20 as of 1.5-7 g and lecithin can be as of 0.3-4 g.

| Formula 3 | | |
|---|---|---|
| Items | Mass (g) | Mass Ratio |
| Fats from either animal parts or plants parts | 6 | 1 |
| Tween 20 | 6-8.5 | 1-1.4 |
| Sunflower lecithin | 4.68-6 | 0.78-1 |
| Citric acid or benzoic acid (optional, not active) | 0.001 or 0 | |

Example 4

Formula 4 with Additional Essential Oil

Formula 4 provides an advantage over Formulas 1 and 2 by blocking the bitterness by adding additional essential oils. Similar to above, 1 g of cannabis oil (either full plant extract or high pure distillate) is added 5 g of formula 2, and the method disclosed above for Formula 1 is used for making the composition.

Each essential oil will have a different synergetic effect on the flavor side with the cannabinoid, which can result in less or more dosage in the final composition. For example, mint oil and ginger oil are so far the best to cover the bitterness flavor from cannabinoid. The ratio of them to cannabinoid can be as low as 2:1. Other essential oils may be applied in a higher quantity to cover the bitterness, which can be over 3:1 or higher. In this formula, Tween 20 range can be more flexible, which can be anywhere from 1.5-5 g, depending on how much quantity of essential oil has been used.

| Formula 4 | | |
|---|---|---|
| Items | Mass (g) | Mass Ratio |
| Olive oil or liquid coconut oil | 0.625 | 1 |
| Tween 20 | 2.5-5.4 | 4-8.64 |
| Sunflower lecithin | 0.625-0.9 | 1-1.44 |
| Citric acid or benzoic acid (optional, not active) | 0.001 or 0 | |
| Spearmint oil, Peppermint oil, Ginger oil, lemon oil, coffee oil, Ylang Ylang oil, raspberry oil, and/or Passion Fruit Oil, any other kinds | 2-4.5 | 3.2-7.2 |

Example 5

Formula 5: Nano-Emulsion for Terpenes or Essential Oils

Formula 5 is robust to mostly any kind of pure or mixed terpenes, which can be either extracted from cannabis plants or other agricultural plants. Some tested terpenes include pinene, limonene, linalool, beta-caryophyllene, myrcene and others. Formula 5 also works to generate any kind of nano-emulsion based on the essential oil. Similar to above, 0.2-1 g of terpenes (either full plant extract or high pure distillate) or 0.2-1 g of essential oil is added with 5 g of formula 2, and the method disclosed above for Formula 1 is used for making the composition.

Since terpenes and essential oils are easier to be made into nano-emulsion compare to cannabinoid, Tween 20 can be used in a slightly wide range from 1.5 g to 5 g. The fats range can be 0.35 g to 2 g and lecithin range can be 0.35 g to 3 g.

| Formula 5 | | |
|---|---|---|
| Items | Mass (g) | Mass Ratio |
| Sunflower oil, Olive oil or other fats | 0.625 | 1 |
| Tween 20 | 2.5-5.4 | 4-8.64 |
| Sunflower lecithin | 0..625-0.9 | 1-1.44 |
| Citric acid or benzoic acid (optional, not active) | 0.001 or 0 | |
| Terpenes or essential oils | 0.2-1 | 0.32-1.6 |

Example 6

Nano-Emulsion Based on 97% CBD Isolate

Formula 6 is developed to not only generate nano-emulsion for 97% CBD isolate, but also block the bitterness of this nano-emulsion. With the composition from Formula 2, nano-emulsion of CBD isolate can be generated. However, in some instances, the bitterness taste may not be desired in food additives. In one embodiment, the inventor found out that the trace amount of polyphenols present in the CBD isolate may contribute to the bitterness. In one embodiment, it was found that the polyphenols are present in the bulk form of the crystals, and when Tween 20 is added, it dissolves the polyphenol out of the system and amplify the bitterness.

To solve this problem, the inventor developed two methods to remove the polyphenols in the system as described below.

Method 1: pre-sonication, dissolve 1 g CBD powder into 10 mL organic solvent such as chloroform, ether or hexane, then wash this organic layer in a separating funnel with 20 mL of 0.01N HCl Solution three times, 20 mL of 5% NaHCO$_3$ three times and saturated NaCl solution 3 times. Then the organic layer was collected, dried with 1-2 g of MgSO$_3$, filtered and then evaporated to dryness. Another washing agent can be 1-3% PVP40 solution: repeat the same wash procedure like above three times with 20 mL of PVP40 solution, then wash with saturated NaCl solution, dried by MgSO$_3$, filtered and then evaporated to dryness. The purified CBD then can be turned into nano-emulsion using formula 2 with much less bitterness.

Method 2: did not treat the CBD raw material but make a nano-emulsion of it with Formula 2, then for every 50 mL of the nano-emulsion, apply 1-10 g of absorbance material to the nano-emulsion as disclosed herein.

Example 7

Formula 7: Nano-Emulsion System with Polyglyceryl-10 Series Surfactants

As further described below, Formula 7 comprises a surfactant from the polyglyceryl-10 series.

| Formula 7 | | |
|---|---|---|
| Items | Mass (g) | Mass Ratio |
| Sunflower oil, Olive oil or other fats | 0.625 | 1 |
| Polyglyceryl-10 Oleate, Polyglyceryl-10 Laurate, Polyglyceryl-10 Caprylate/Caprate or Polyglyceryl Ester Fatty Acid (POLYALDO ® 10-2-P) | 1.95-2.5 | 3.12-4 |
| Sunflower lecithin or purified lecithin | 0.625-0.9 | 1-1.44 |
| Citric acid or benzoic acid (optional, not active) | 0.001 or 0 | |

Polyglyceryl-10 series surfactants are not only very safe to consume, but they also present better surface activity in making cannabinoid nanoemulsions. Especially for Polyglyceryl-10 Oleate, Polyglyceryl-10 Laurate, Polyglyceryl-10 Caprylate/Caprate and Polyglyceryl Ester Fatty Acid (POLYALDO® 10-2-P), they can used in less amount compared to Tween series surfactants to generate cannabinoid nanoemulsion. Sometimes, due to the surfactants' own milky colors, the finished nanoemulsion appears to be milky/translucent instead of fully transparent. Polyglyceryl-10 series surfactants can be used together with sunflower lecithin or purified lecithin for nanoemulsion generation. Due to the safety nature of Polyglyceryl-10 series surfactants and lecithin, this combination may have huge potential applications as premium food/drink ingredients.

Example 8

Boundary Conditions

In one embodiment, the main building blocks within each formula comprise carrier oil, tween 20 or tween 80 and Sunflower lecithin. For every 1 g of cannabinoid oil used, carrier oil's range should be within 0.25 g to 8 g, Tween 20 or Tween 80 range should be within 2.5 g to 8 g, and sunflower lecithin should be within the range of 0.3 g to 4 g.

If other essential oils are used to block the flavor, mint oil works the best as masking the bitterness, while lemon oil takes advantage its own natural bitterness to cover the cannabinoid bitterness. So of the essential oils may be needed at least 2-3 times higher mass than cannabinoid oils' mass.

Some other surfactant types may not work as good as the combination of tween 20/tween 80 with Sunflower lecithin. For example, soy derived lecithin is a solid wax, it does not work as well as sunflower lecithin. Also, surfactants like Span 80, Span 20 works with the combination of Tween 20 or Tween 80, but not used as primary surfactant by themselves. Surfactants like Glyceryl Laurate, PolyGlyceryl 3-Laurate, PolyGlyceryl 3-Oleate and Glyceryl Stearate Citrate often offer a cloudy emulsion with droplet size in the range over 200 nm. They can be used in the case where nano-size is not required. Thus, they are not used directly in the formula disclosed herein.

The power of converting hydrophobic materials into water soluble nano-emulsion also helps recombine and regenerate the desired final aqueous product, some of those can be found in natural material, some of them can be simulated in a way which has never been explored from natural compounds. For example, by adding 4 parts of full plant CBD nano-emulsion with 1 part of linalool nano-emulsion and 2 parts of limonene nano-emulsion, a synthetic drink can be generated. It can quickly ease the nerve and calm people down with a very mild brain reaction. This combination can not be found in nature, and the nano-emulsion formula enabled unlimited discovery like this.

Example 9

Small Molecule Food Emulsifiers with HLB<7

In one embodiment, the inventor unexpectedly and surprisingly found that while Span 20 resulted in a nano-emulsion having average particle size of less than 100 nm, Span 40, Span 60, Span 80, Span 83, Span 85, and Span 120 resulted in nano-emulsions having average particle size of more than 100 nm. In this example, 1 g of cannabinoid, 0.625 g of olive oil, 3.75 g of Tween 80, and different kinds of Span surfactant were used to make the composition. Thus, in each case, Span to Tween 80 is at mass ratio of 1:6. The 80% amplitude of sonication was applied to 45 mL of total volume of mixed liquid with Span, Tween 80, carrier oil, cannabinoid oil and water. Droplet size change was monitored by DLS time wise. Sonication was stopped when droplet size reach plateau and does not decrease.

The table shows that only Span 20 can generate emulsion that have droplet size smaller than 100 nm. With decrease HLB of Span surfactant, the droplet size increases. Even though most of Span surfactants failed to make nanoemulsion, but they may be utilized when a larger droplet sized emulsion is desired.

| Span Surfactants | HLB | Final Emulsion droplet average size (nm) |
|---|---|---|
| Span 20 | 8.6 | 91 |
| Span 40 | 6.7 | 245 |
| Span 60 | 4.7 | 316 |
| Span 80 | 4.3 | 387 |
| Span 83 | 3.7 | 560 |
| Span 85 | 1.8 | 876 |
| Span 120 | 4.7 | 302 |

Example 10

Lecithin

As described throughout this application, lecithin may be used as a co-surfactant in the composition disclosed herein. In one embodiment, the inventor found that unexpectedly and unanticipatedly, natural lecithin from Soy does not work in the composition while natural lecithin from Sunflower works! Natural lecithin from Sunflower is a viscous dark brown liquid; it is easier to dissolve in the cannabinoid+carrier oil+main surfactant system. In example 1, together with Tween 80, it can generate emulsion with average droplet size of 40-50 nm. However, natural lecithin from Soy it takes longer to dissolve into the cannabinoid+carrier oil+main surfactant system. And with adding water, some of it precipitated out. It needed longer time to get it back into a homogenous system. Soy lecithin, together with Tween 80, cannabinoid oil, edible oil, and water could generate emulsion with average droplet size of 150-170 nm, but could not generate a nano-emulsion with average droplet size of less than 100 nm.

Example 11

Amount of Water

In another embodiment, the inventor unexpectedly discovered that the amount of water in the composition is important for the droplet size. The inventor found that when the amount of water in the composition is less than 1.15 times the combination amount of cannabinoid oil, carrier oil, main surfactant and co-surfactant, the resulting emulsion has a droplet size of more than 100 nm.

For example, when 10 g of cannabinoid, 6.25 g of olive oil, 37.5 g of Tween 80, and 6.25 g of sunflower lecithin was mixed with different amounts of water and sonicated as described, the final emulsion droplet average size varied as shown below in the chart.

| Water amount | Cannabinoid concentration in final emulsion (mg/g) | Final Emulsion droplet average size (nm) |
|---|---|---|
| 70 | 76.92 | 197 |
| 90 | 66.67 | 124 |
| 120 | 55.56 | 98 |
| 170 | 43.48 | 64 |
| 250 | 32.26 | 41 |

Thus, when the amount of the other ingredients is kept the same, and the amount of water was varied, the more water there is, the smaller the droplet size. In other words, if the final cannabinoid concentration in the starting emulsion is more than 65 mg/g, then the starting emulsion may not have a nanosized droplet.

Example 12

Stability of the Composition

In another surprising result, the inventor found that in system 4, when there is no co-surfactant as of natural lecithin, purified lecithin, or small molecule food emulsifiers, the main surfactant can make nano-emulsion with average size of 50 nm. However, the nano-emulsion made by such a process does not have long term stability. In an elevated temperature (55° C. Oven) stability study, the droplet size of the nano-emulsion increases from 50 nm to 150 nm in 2 weeks, and to 300 nm in 5 weeks and to 620 nm in 8 weeks. At week 8, it becomes a little bit opaque. So, without co-surfactant, system 4 can generate a nano-emulsion, but its stability dramatically decreases compared to other systems with co-surfactant. On the other hand, when a co-surfactant is present, the composition had long term stability—12 weeks no layer separation in 55° C. Oven.

For all the examples above, and for all formula combinations mentioned in this disclosure, water amount can be varied dramatically as long as it is 1.15 times higher than the amount of combination of cannabinoid oil, carrier oil and surfactant systems. This indicates the final concentration of the cannabinoid in the finished emulsion can vary from ~60-70 mg/g down to very low as of 0.01 mg/g, in which case excess amount of water is added. It means all the formula combinations in this disclosure can not only make concentration nanoemulsion that can be diluted later into food or cosmetic, they can also generate end product with variable targeted concentrations.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A storage stable beverage containing a nano-emulsion composition, comprising:
   a cannabinoid oil, a dietically acceptable carrier oil, a main surfactant, a co-surfactant, and water that form the nano-emulsion composition;
   wherein the main surfactant is selected from a group consisting of Polyglyceryl-10 Dipalmitate, Polyglyceryl-10 Oleate, Polyglyceryl-10 Laurate, and Polyglyceryl-10 Caprylate/Caprate;
   wherein the co-surfactant is a natural lecithin, a purified lecithin, or a combination thereof;
   wherein the amount of water is at least 1.15 times the amount of the combination of the cannabinoid oil, the dietically acceptable carrier oil, and the main surfactant;
   wherein the amount of the dietically acceptable carrier oil is at least 0.3 times the amount of the cannabinoid oil; and
   wherein the amount of the main surfactant is at least 1.45 times the amount of cannabinoid oil, and/or wherein the amount of main surfactant is at least 1.35 times the amount of the dietically acceptable carrier oil, and/or wherein the amount of main surfactant is at least 1.15 times the amount of combination of cannabinoid oil and the dietically acceptable carrier oil;
   wherein an average droplet size in the nano-emulsion is less than 200 nm;
   wherein the nano-emulsion composition remains in dispersed form and the droplet size remains unaffected upon dilution in an aqueous solution to thereby form the beverage; and
   wherein the beverage can be stored at room temperature for at least 6 months without change in the droplet size.

2. The beverage containing the nano-emulsion composition of claim 1, wherein the natural lecithin is derived from soybean, eggs, milk, marine sources, rapeseed, cottonseed, or sunflower.

3. The beverage containing the nano-emulsion composition of claim 1, wherein the purified lecithin comprises natural and hydrogenated lecithin fractions and phospholipids from egg, soybean, rapeseed, or sunflower, or phosphatidylcholine.

4. The beverage containing the nano-emulsion composition of claim 1, wherein if the co-surfactant is a natural lecithin, then the amount of the co-surfactant is at least 0.75 times the amount of the dietically acceptable carrier oil; and wherein if co-surfactant is a purified lecithin, then the amount of the co-surfactant is at least 0.50 times the amount of the dietically acceptable carrier oil.

5. The beverage containing the nano-emulsion composition of claim 1, wherein the cannabinoid oil comprises a phytocannabinoid.

6. The beverage containing the nano-emulsion composition of claim 5, wherein the phytocannabinoid is selected from Tetrahydrocannabinolic acid A, Tetrahydrocannabinolic acid B, Tetrahydrocannabinol, Tetrahydrocannabinolic acid C, Tetrahydrocannbinol C, Tetrahydrocannabivarinic acid, Tetrahydrocannabivarin, Tetrahydrocannabiorcolic acid, Tetrahydrocannabiorcol, Delta-7-cis-iso-tetrahydrocannabi varin, A-tetrahydrocannabinolic acid, A-tetrahydrocannabinol, Cannabidiolic Acid, Cannabidiol, Cannabidiol monomethyl ether, Cannabidiol-C, Cannabidivarinic Acid, Cannabidivarin, Cannabidiorcol, Cannabigerolic Acid, Cannabigerolic Acid monomethylether, Cannabigerol, Cannabigerolmonomethylether, Cannabigerovarinic Acid, Cannabigerovarin, Cannabichromenic Acid, Cannabichromene, Cannabichromevarinic Acid, Cannabichromevarin, Cannabicyclolic acid, Cannabicyclol, Cannabicyclovarin, Cannabielsoic acid A, Cannabielsoic acid B, Cannabielsoin, Cannabinolic acid, Cannabinol, Cannabinol methylether, Cannabinol-C, Cannabivarin, Cannabino-C, Cannabiorcol, Cannabinodiol, Cannabinodivarin, Cannabitriol, 10-Ethoxy-9-hydroxy-4-tetrahydrocannabinol, 8.9-Dihydroxy-4-tetrahydrocannabinol, Cannabitriolvarin, Ethoxy-cannabitriolvarin, Dehydrocannabifuran, Cannbifuran, Cannabichromanon, Cannabicitran, 10-Oxo-4-tetrahydrocannabinol, A-cis-tetrahydrocannabinol, Cannabiripsol, 3,4,5,6-tetrahydro-7-hydroxy-alpha-alpha-2-trim ethyl-9-n-propyl-2, 6-methano-2H-1-benzoxocin-5-methanol, Trihydroxy-delta-9-tetrahydrocannabinol, Isocanabinoids, and Epigallocatechin gallate, or combinations thereof.

7. The beverage containing the nano-emulsion composition of claim 1, wherein the dietically acceptable carrier oil is an oil derived from plants, selected from the group consisting of sunflower oil, olive oil, coconut oil, sesame oil, avocado oil, palm oil, soybean oil, corn oil, peanut oil, canola oil, grape seed oil, corn oil, hazelnut oil, rice bran oil, linseed oil, safflower oil, sesame oil, passion fruit oil or combinations thereof.

8. The beverage containing the nano-emulsion composition of claim 1, wherein the composition further comprises one or more preservatives.

9. The beverage containing the nano-emulsion composition of claim 8, wherein the preservative is selected from the group consisting of ethyl lauroylarginate, sodium bisulphite, potassium benzoate, potassium sorbate, ascorbic acid, citric acid, benzoic acid, sodium benzoate, calcium ascorbate, erythorbic acid, sodium ascorbate, sorbic acid, sulphurous acid, calcium sorbate, Vitamin C, Vitamin E, and combinations thereof.

10. The beverage containing the nano-emulsion composition of claim 1, wherein the composition further comprises a flavoring agent.

11. The beverage containing the nano-emulsion composition of claim 10, wherein the flavoring agent is an essential oil, a bitter blocker or a terpene.

12. The beverage containing the nano-emulsion composition of claim 11, wherein the essential oil is lemon oil, orange oil, peppermint oil, spearmint oil, YlangYlang oil, Lemon Grass oil, Tea Tree oil, Rosemary oil, Australian Sandalwood oil, Grape fruit oil, frankincense oil, cedarwood oil, patchouli oil, cinnamon bark oil, bergamot oil, chamomile oil, Lemon Eucalyptus oil, ginger oil, key lime oil, vanilla oil or clove oil.

13. The beverage containing the nano-emulsion composition of claim 11, wherein the terpene is Alpha-Pinene, Linalool, Myrcene, Limonene, Ocimene, Terpinolene, Terpineol, Valencene, Beta-Caryophyllene, Geraniol, Humulene, Pulegone, Phellandrene, Carene, Terpinene, Fenchol, Borneol, Bisabolol, Phytol, Camphene, Sabinene, Camphor, Isoborneol, Menthol, Cedrene, Nerolidol, Guaiol, Isopulegol, Geranyl Acetate, Cymene or Eucalyptol.

14. The beverage containing the nano-emulsion composition of claim 1, wherein the beverage has a pH between 2.5 and 8.0.

15. A nano-emulsion composition consisting essentially of:
- a cannabinoid oil, a dietically acceptable carrier oil, a main surfactant, a co-surfactant, and water;
  - wherein the main surfactant is selected from a group consisting of Polyglyceryl-10 Dipalmitate, Polyglyceryl-10 Oleate, Polyglyceryl-10 Laurate, and Polyglyceryl-10 Caprylate/Caprate;
  - wherein the co-surfactant is a natural lecithin, a purified lecithin, or a combination thereof;
  - wherein the amount of water is at least 1.15 times the amount of the combination of the cannabinoid oil, the dietically acceptable carrier oil, and the main surfactant;
  - wherein the amount of the dietically acceptable carrier oil is at least 0.3 times the amount of the cannabinoid oil; and
  - wherein the amount of the main surfactant is at least 1.45 times the amount of cannabinoid oil, and/or wherein the amount of main surfactant is at least 1.35 times the amount of the dietically acceptable carrier oil, and/or wherein the amount of main surfactant is at least 1.15 times the amount of combination of cannabinoid oil and the dietically acceptable carrier oil; and
- wherein an average droplet size in the nano-emulsion is less than 200 nm;
- wherein the nano-emulsion composition remains in dispersed form and the droplet size remains unaffected upon dilution in an aqueous solution to thereby form a beverage.

\* \* \* \* \*

UNITED STATES PATENT AND TRADEMARK OFFICE
CERTIFICATE OF CORRECTION

PATENT NO. : 11,013,715 B2  
APPLICATION NO. : 16/206869  
DATED : May 25, 2021  
INVENTOR(S) : Chunxiao Han Page 1 of 1

It is certified that error appears in the above-identified patent and that said Letters Patent is hereby corrected as shown below:

In the Claims

In Column 24, Lines 19-20, Claim 6 the text "10-Ethoxy-9-hydroxy-4-tetrahydrocannabinol" should be replaced with "10-Ethoxy-9-hydroxy-Δ-tetrahydrocannabinol"

In Column 24, Lines 20-21, Claim 6 the text "8.9-Dihydroxy-4-tetrahydrocannabinol" should be replaced with "8,9-Dihydroxy-Δ-tetrahydrocannabinol"

In Column 24, Line 23, Claim 6 the text "10-Oxo-4-tetrahydrocannabinol" should be replaced with "10-Oxo-Δ-tetrahydrocannabinol"

Signed and Sealed this  
Twenty-seventh Day of July, 2021

Drew Hirshfeld  
*Performing the Functions and Duties of the*  
*Under Secretary of Commerce for Intellectual Property and*  
*Director of the United States Patent and Trademark Office*